United States Patent [19]

Nakamura et al.

[11] Patent Number: 4,710,373

[45] Date of Patent: Dec. 1, 1987

[54] LONG WAVELENGTH ULTRAVIOLET RAY ABSORBER

[75] Inventors: Koichi Nakamura, Ichikaimachi; Michihiro Hattori, Utsunomiya; Tadashi Tamura, Ichikaimachi; Toru Tejima, Kokubunjimachi; Naotake Takaishi; Genji Imokawa, both of Utsunomiya; Hajime Hotta, Funabashi, all of Japan

[73] Assignee: Kao Corporation, Tokyo, Japan

[21] Appl. No.: 710,714

[22] Filed: Mar. 12, 1985

[30] Foreign Application Priority Data

Mar. 12, 1984 [JP]  Japan ................... 59-46850

[51] Int. Cl.$^4$ .............. A61K 7/021; A61K 7/027; A61K 7/42; A61K 9/10
[52] U.S. Cl. .................. 424/59; 424/DIG. 5; 424/47; 424/63; 424/64; 424/69; 514/845; 514/846; 514/937; 514/938; 514/941
[58] Field of Search ............... 424/59, 60; 568/333; 514/846

[56] References Cited

U.S. PATENT DOCUMENTS 4,381,360  4/1983  Leistner et al. ............... 524/396
4,489,057  12/1984  Welters et al. ............... 424/59

FOREIGN PATENT DOCUMENTS 962597   2/1975  Canada ..................... 424/59
0072142  2/1983  European Pat. Off. ......... 424/59
3314568  10/1984 Fed. Rep. of Germany ...... 424/59
2506156  11/1952 France ......................... 59/
1216501  11/1959 France ......................... 424/59
47-42502 10/1972 Japan .......................... 424/59
0172415  9/1984  Japan .......................... 424/59
341992   1/1931  United Kingdom ............. 424/59
1387281  3/1975  United Kingdom ............. 424/59
1473483  5/1977  United Kingdom ............. 424/59
2081716  2/1982  United Kingdom ............. 424/59
2098868  12/1982 United Kingdom ............. 424/59

OTHER PUBLICATIONS

Troeltzsch, Chem. Abs., 1964, vol. 60, p. 7947e.
Wurm et al, Chem. Abs., 1977, vol. 87, p. 22971r.
Yamane et al, Chem. Abs., 1960, vol. 56, p. 9416f.
Tolmachev et al, Chem. Abs., 1968, vol. 69, p. 106444n.
DeMent Abstract, O.G. 10/28/52, vol. 663, p. 1221.
Geissler et al, Chem. Abs; 1983, vol. 98, 174687t.

Primary Examiner—Dale R. Ore
Attorney, Agent, or Firm—Oblon, Fisher, Spivak, McClelland & Maier

[57] ABSTRACT

A composition for application to the skin to protect the skin from the long wavelength ultraviolet ray comprises a dibenzoylmethane derivative of the following general formula

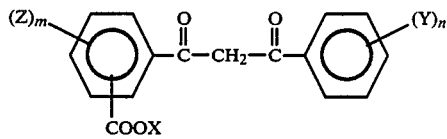

in which X represents a hydrogen atom, a monovalent metal cation, an organic cation, a linear or branched alkyl group having from 1 to 24 carbon atoms, or a polyoxyalkylene oxide having 2 or 3 carbon atoms, Y and Z each independently represent a hydroxyl group, a linear or branched alkyl group having from 1 to 24 carbon atoms, or an alkoxy group having from 1 to 24 carbon atoms, or a polyoxyalkylene oxide group having from 2 to 3 carbon atoms, and m and n are independently an integer of from 0 to 3.

The composition is adjustable so as to have an optimum HLB balance and has good compatibility with various cosmetic bases. Further, it does not irritate the skin, is difficult to be percutaneously absorbed and shows continued skin-protecting effects.

5 Claims, 8 Drawing Figures

FIG. 6-A
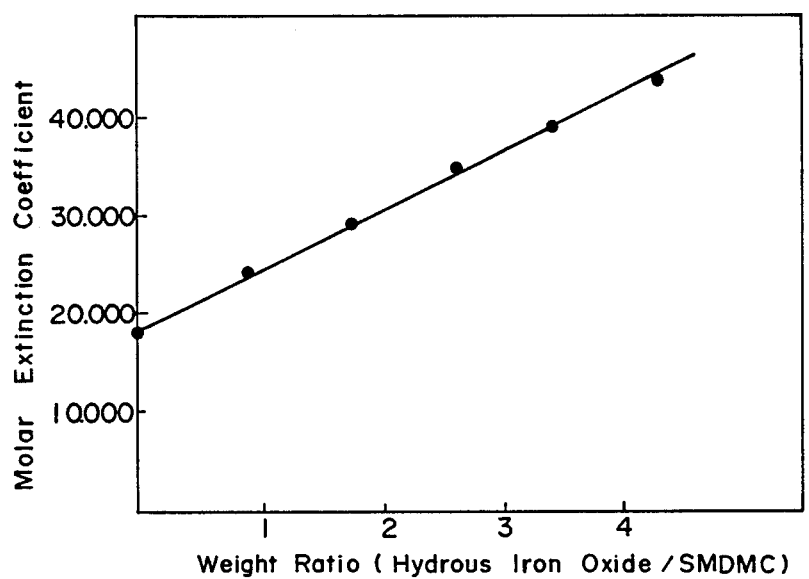
FIG. 6-B
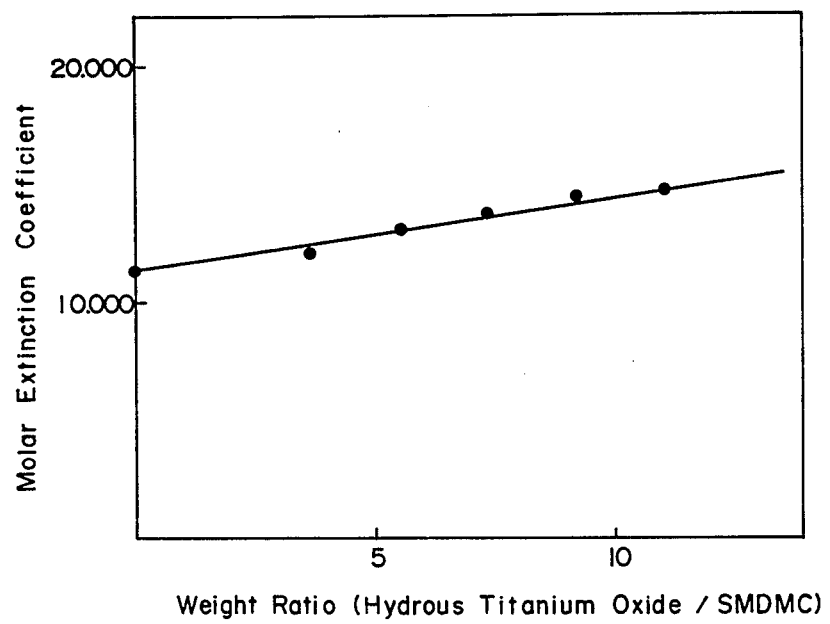

LONG WAVELENGTH ULTRAVIOLET RAY ABSORBER

BACKGROUND OF THE INVENTION (i) Field of the Invention:

This invention relates to long wavelength ultraviolet ray absorbers (hereinafter referred to simply as UV absorbers) and more particularly, to UV absorbers comprising dibenzoylmethane derivatives having one carboxylic acid, a carboxylate or a carboxylic acid ester group in each benzene ring thereof with or without hydrous oxides of polyvalent metallic elements.

(ii) Description of the Prior Art:

Ultraviolet rays are known to cause various dermatological effects on the skin. Dermatologically, ultraviolet rays are divided into a long wavelength ultraviolet ray having a wavelength of from 400 to 320 nm, a medium wavelength ultraviolet ray having a wavelength of from 320 to 290 nm, and a short wavelength ultraviolet ray having a wavelength not larger than 290 nm, which are, respectively, called UV-A, UV-B and UV-C.

Sunlight is a main ultraviolet ray source to which men are ordinarily exposed. Ultraviolet rays in the sunlight which arrive at the earth are UV-A and UV-B. UV-C is absorbed in the ozone layer and rarely reaches the earth. Of the UV rays which arrive at the earth, UV-B serves to form erythema and blisters when irradiated on the skin over a certain level of exposure. In addition, melanogenesis, which leads to pigmentation, is accelerated. In contrast, UV-A was believed not to cause any substantial changes in the skin. In recent years, however, it has been revealed through electron-microscopic and histological techniques that the skin suffers dermatological changes by irradiation of UV-A. In particular, the energy of UV-A arrives even at the inner skin as is different from UV-B and thus causes elastic fibers in the blood vessel walls and connective-tissue membranes to be affected slightly chronically. These changes are considered to lead to the promotion of senility of the skin. Moreover, it is also known that UV-A has the action of melanizing the skin immediately after the irradiation thereof (immediate pigmentation) and increases the degenerating action of UV-B on the skin. Thus, UV-A is considered to be one of main factors of producing or exacerbating moth-patches or freckles on the face.

As will be appreciated from the above, it is important to protect the skin not only from UV-B, but also from UV-A in order to prevent aging, moth-patches, and freckles on skin from being produced or exacerbated.

However, studies on the action of UV-A on the skin have just started and thus few substances effectively absorbing UV-A upon application to the skin have been known. Currently known substances are only dibenzoylmethane derivatives and cinnamic acid derivatives, most of which are liposoluble (West Germany Published Pat. Nos. 2728241 and 2728243, Japanese Laid-open Patent Application Nos. 51-61641, 52-46056 and 57-197209). Only a few are soluble in water (Japanese Laid-open Patent Application No. 57-59840).

If it is intended to add these UV-A absorbers to cosmetics, limitations are placed on the properties of a cosmetic substrate. Accordingly, there is a demand for a development of more widely usable UV-A absorbers. Such UV-A absorbers should satisfy the following requirements.

(1) A maximum absorption wavelength in the vicinity of 350 nm.

(2) A sufficiently high molar extinction coefficient ($\epsilon$) at the above-indicated wavelength.

(3) A small absorbance in the visible light range because coloration as cosmetic compositions is not desirable, i.e. $\epsilon=0$ over 400 nm.

(4) Good stability against heat and light.

(5) No toxic, irritative and other noxious actions on the skin.

(6) Good compatibility with cosmetic substrates.

(7) Difficulty in percutaneous absorption and in removal such as by perspiration upon application to the skin, with the effects of the absorber being effectively lasted.

(8) Inexpensiveness.

Moreover, there is also a demand of a development for UV absorbers which are effective not only for UV-A, but also for UV-B. Such UV-absorbers should satisfy, aside from the above requirements (1) through (8), the requirement that they have a maximum absorption in the vicinity of 290 nm.

SUMMARY OF THE INVENTION

Under these circumstances, the present inventors made intensive studies and, as a result, found that dibenzoylmethane derivatives having specific substituents can satisfy all the requirements with regard to UV-A absorbers.

It was also found that the dibenzoylmethane derivatives used in combination with hydrous oxides of polyvalent metallic elements were able to absorb not only UV-A, but also UV-B.

In accordance with one embodiment of the invention, there is provided a long wavelength ultraviolet ray absorber which comprises a dibenzoylmethane derivative of the following general formula

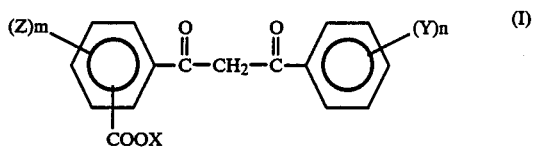

in which X represents a hydrogen atom, a monovalent metal cation, an organic cation, a linear or branched alkyl group having from 1 to 24 carbon atoms, or a polyoxyalkylene oxide having 2 or 3 carbon atoms, each Y and each Z independently represent a hydroxyl group, a linear or branched alkyl group having from 1 to 24 carbon atoms, or an alkoxy group having from 1 to 24 carbon atoms, or a polyoxyalkylene oxide group having from 2 to 3 carbon atoms, and m and n are independently an integer of from 0 to 3.

The UV absorber may further comprise, aside from the dibenzoylmethane derivative (I), hydrous oxides of polyvalent metallic elements.

BRIEF DESCRIPTION OF THE DRAWINGS

FIG. 6 is a graph showing a molar extinction coefficient of SMDMC mixed with hydrous iron oxide or hydrous titanium oxide in relation to ratio by weight of each oxide to SMDMC;

Figure 1:
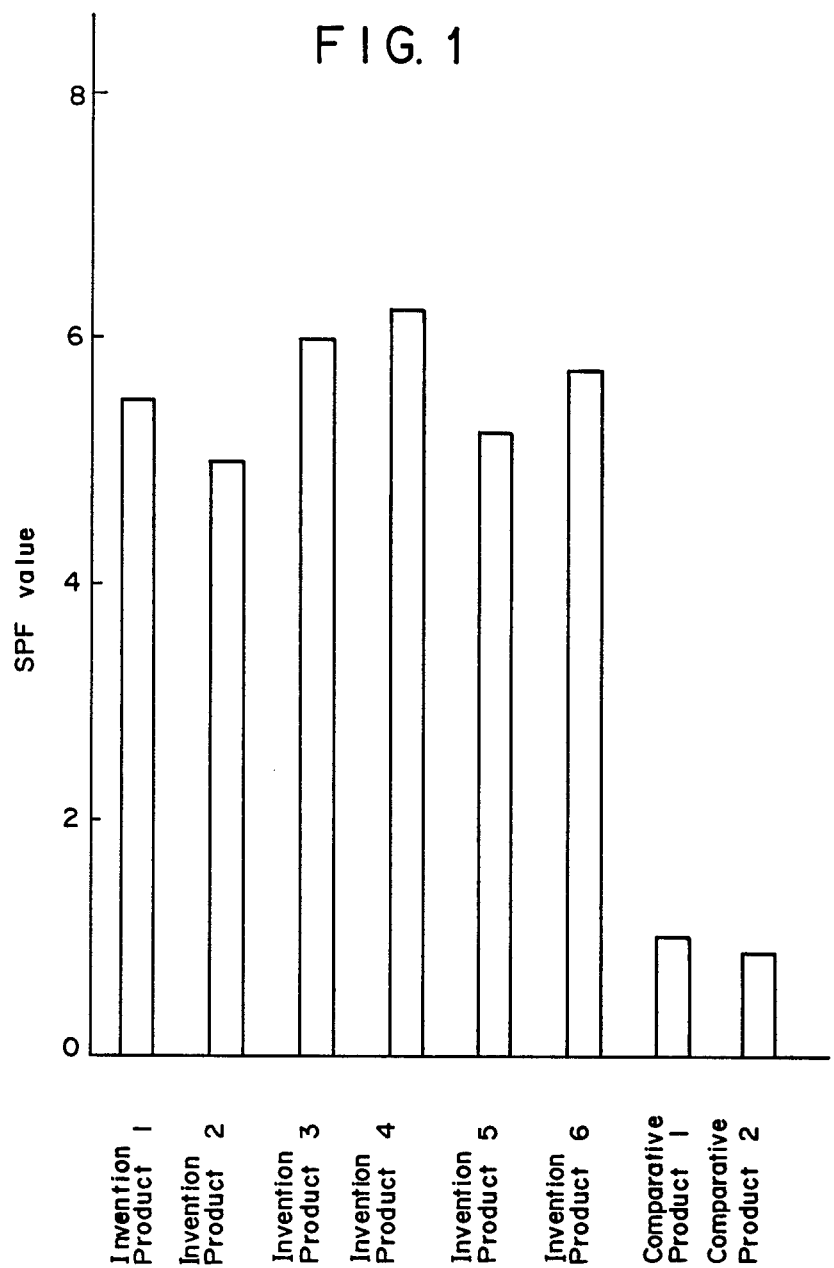
FIG. 1 is a graph showing SPF values of the absorber products 1 through 6 of the invention and comparative products 1 and 2.

DETAILED DESCRIPTION OF THE INVENTION AND PREFERRED DESCRIPTION OF THE EMBODIMENTS

In the formula (I), X represents a hydrogen atom, a monovalent metal cation, or an organic cation. Examples of the monovalent metal cation include sodium, potassium, lithium and the like, and examples of the organic cation include arginine, trimethylethanolamine and the like.

The dibenzoylmethane derivatives of the general formula (I) are prepared by known processes including, for example, processes described in Ann. Chim. (Rone), 48, 762(1958), J. Chem. Soc., 2063(1952), Pestic Sci., 4, 473(1973), and U.S. Pat. No. 4,381,360.

The simplest process is a process which comprises subjecting a monoester of substituted phthalic acid (including all isomers such as ortho, meta and para isomers) having the following formula (II) to condensation reaction with substituted acetophenone of the formula (III) in the presence of a base according to the following reaction formula, thereby obtaining a compound of the formula (Ia), and treating the compound (Ia) by a usual manner to obtain an intended salt or ester

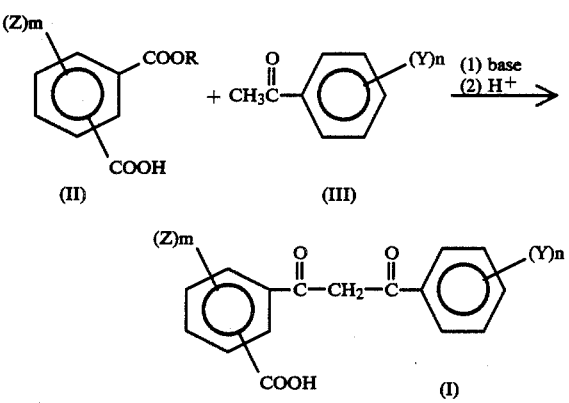

in which R represents a methyl group or an ethyl group, and Y, Z, m and n have, respectively, the same meanings as defined before.

If ortho phthalic acid is used in the above process, an acid anhydride of the following general formula (IV) may be used instead of the monoester (II)

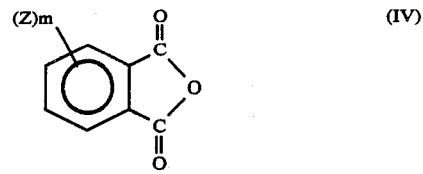

in which Z and m have, respectively, the same meanings as defined before.

The dibenzoylmethane derivatives of the general formula (I) may be divided into the following groups.

(1) Dibenzoylmethanecarboxylic acids or salts of the general formula (V)

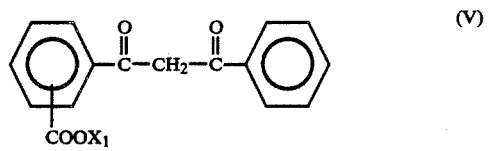

in which $X_1$ represents a hydrogen atom, a monovalent metal cation, or an organic cation, and the position of the substituent, $-COOX_1$, is an ortho, meta or para position.

(2) 4'-alkoxydibenzoylmethanecarboxylic acids or salts of the general formula (VI)

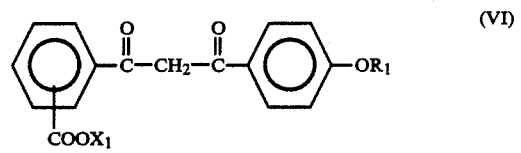

in which $R_1$ represents a hydrogen atom, or a hydrocarbon group having from 1 to 18 carbon atoms, preferably a linear or branched alkyl or alkylene group having from 1 to 4 carbon atoms, and the position of the substituent, $-COOX_1$, and $X_1$ are, respectively, the same as defined before.

(3) 3'-hydroxy-4'-alkoxydibenzoylmethanecarboxylic acids or salts of the general formula (VII)

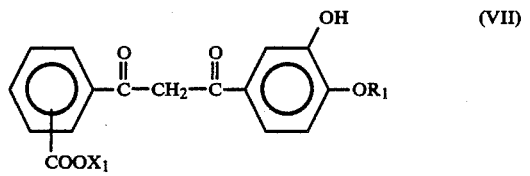

in which the position of the substituent, $-COOX_1$, $X_1$, and $R_1$ are, respectively, the same as defined before.

(4) 2,3'-dihydroxy-4'-alkoxydibenzoylmethanecarboxylic acids or salts of the formula (VIII)

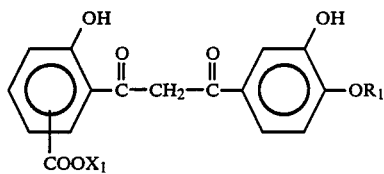
(VIII)

in which the position of the substituent, —COOX$_1$, X$_1$, and R$_1$ have, respectively, the same meanings as defined before.

(5) 4'-Alkoxy-2-polyoxyethyleneoxydibenzoylmethanecarboxylic acids or salts of the following formula (IX)

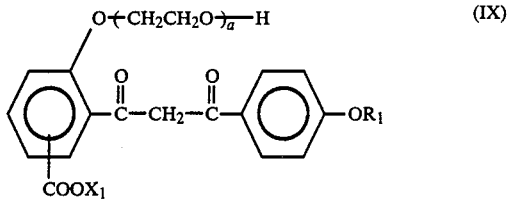
(IX)

in which the position of the substituent, —COOX$_1$, X$_1$, and R$_1$ are, respectively, the same as defined before, and a is an integer of from 1 to 10, preferably from 1 to 6.

(6) 3',4'-bis(polyoxyethyleneoxy)-dibenzoylmethanecarboxylic acids or salts of the general formula (X)

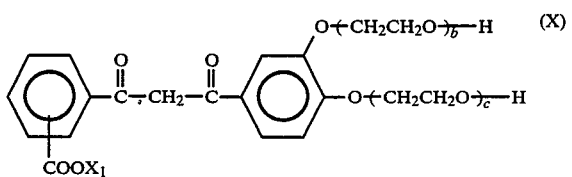
(X)

in which the position of the substituent, —COOX$_1$, and X$_1$ are, respectively, the same as defined before, and b and c are independently an integer of from 1 to 6, preferably 1 to 3.

(7) 4'-Polyoxyethyleneoxydibenzoylmethanecarboxylic acids or salts of the general formula (XI)

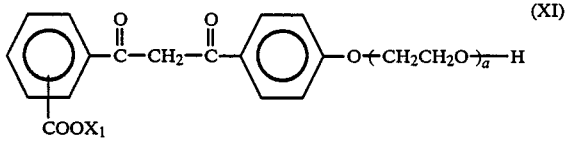
(XI)

in which the position of the substituent, —COOX$_1$, X$_1$, and a are, respectively, the same as defined before.

(8) 4'-Alkoxy-3'-polyoxyethyleneoxydibenzoylmethanecarboxylic acids or salts of the general formula (XII)

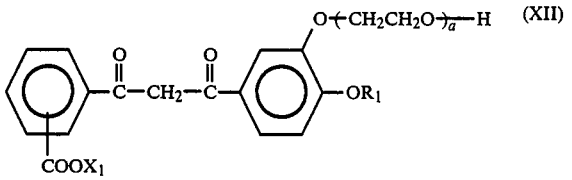
(XII)

in which the position of the substituent, —COOX$_1$, X$_1$, R$_1$, and a are, respectively, the same as defined before.

(9) 4'-Alkoxy-4-alkyldibenzoylmethanecarboxylic acid alkyl esters of the general formula (XIII)

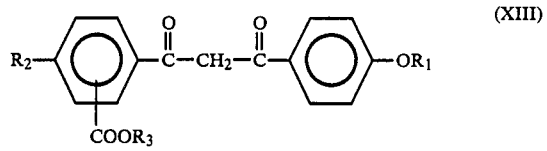
(XIII)

in which R$_2$ and R$_3$ independently represent a linear or branched alkyl or alkylene group having from 1 to 24 carbon atoms, preferably from 1 to 18 carbon atoms, the position of the substituent, —COOR$_3$, is an ortho or meta position, and R$_1$ has the same meaning as defined before.

(10) 3',4'-Dialkoxydibenzoylmethanecarboxylic acid alkyl esters of the general formula (XIV)

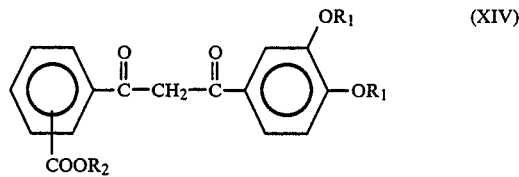
(XIV)

in which the position of the substituent, —COOR$_2$, is an ortho, meta or para position, and R$_1$ and R$_2$ have, respectively, the same meanings as defined before.

(11) 3',4'-Bis(polyoxypropyleneoxy)dibenzoylmethanecarboxylic acid alkyl esters of the general formula (XV)

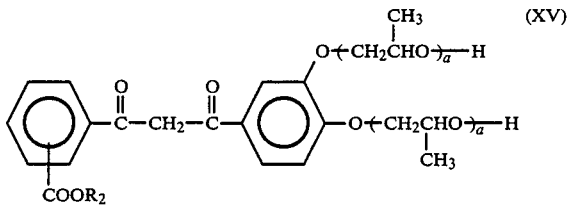
(XV)

in which the position of the substituent, —COOR$_2$, and a have, respectively, the same meaning as defined before.

(12) 2,3'-Dialkoxy-4'-polyoxypropyleneoxydibenzoylmethanecarboxylic acid alkyl esters of the general formula (XVI)

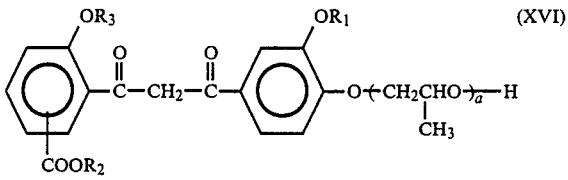
(XVI)

in which the position of the substituent, —COOR$_2$, R$_1$, R$_2$, and a have, respectively, the same meanings as defined before.

(13) 2,3',4'-Trialkoxydibenzoylmethanecarboxylic acid alkyl esters of the general formula (XVII)

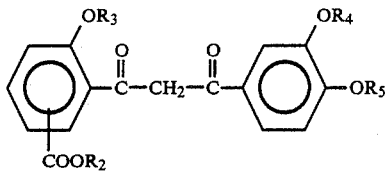

(XVII)

in which $R_4$ and $R_5$ independently represent a linear or branched alkyl or alkylene group having from 1 to 24 carbon atoms, preferably from 1 to 18 carbon atoms, and the position of the substituent, $-COOR_2$, $R_2$, and $R_3$ have, respectively, the same meanings as defined before.

(14) 4'-Alkoxydibenzoylmethanecarboxylic acid alkyl esters of the general formula (XVIII)

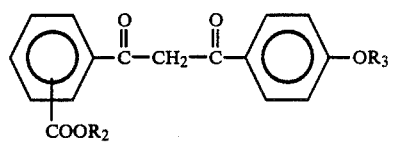

(XVIII)

in which the position of the substituent, $-COOR_2$, $R_2$, $R_3$, and $R_4$ have, respectively, the same meanings as defined before.

(15) 2',4'-Dialkoxydibenzoylmethanecarboxylic acid alkyl esters of the general formula (XIX)

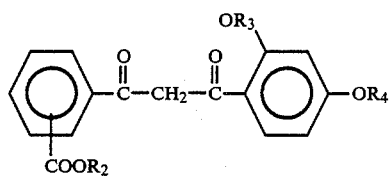

(XIX)

in which the position of the substituent, $-COOR_2$, $R_2$, $R_3$, and $R_4$ have, respectively, the same meanings as defined before.

(16) 4'-Alkyldibenzoylmethanecarboxylic acid alkyl esters of the general formula (XX)

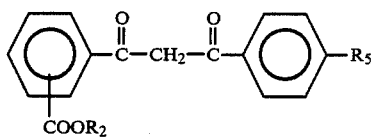

(XX)

in which $R_5$ represents a hydrogen atom, or a linear or branched alkyl group having from 1 to 24 carbon atoms, and the position of the substituent, $-COOR_2$, and $R_2$ are, respectively, the same as defined before.

Among the dibenzoylmethane derivatives, compounds which are soluble in water include, for example, dibenzoylmethane-2-carboxylic acid trimethylethanolamine salt, sodium dibenzoylmethane-3-carboxylate, sodium 4'-methoxydibenzoylmethane-2-carboxylate, sodium 4'-methoxydibenzoylmethane-3-carboxylate, 3'-hydroxy-4'-methoxydibenzoylmethane-2-carboxylic acid, sodium 2,3'-dihydroxy-4'-methoxybenzoylmethane-5-carboxylic acid, potassium 4'-methoxy-2-polyoxyethyleneoxydibenzoylmethane-5-carboxylate, sodium 3',4'-bis(polyoxyethyleneoxy)-dibenzoylmethane-3-carboxylate, potassium 4'-methoxydibenzoylmethane-4-carboxylate, sodium 4'-polyoxyethyleneoxydibenzoylmethane-4-carboxylate, potassium 4'-methoxy-3'-polyoxyethyleneoxydibenzoylmethane-4-carboxylate, and the like. Examples of the derivative compounds which are fat-soluble include 4'-methoxy-4-1 methyldibenzoylmethane-2-carboxylic acid isostearyl ester, 3',4'-dimethoxydibenzoylmethane-2-carboxylic acid oleyl ester, 3',4'-bis(polyoxypropoxy)dibenzoylmethane-2-carboxylic acid methyl ester, 2,3'-dimethoxy-4'-polyoxypropyleneoxydibenzoylmethane-5-carboxylic acid hexyl ester, 3',4'-dihexyloxy-2-methoxydibenzoylmethane-5-carboxylic acid butyl ester, 4'-tetracosyloxydibenzoylmethane-3-carboxylic acid methyl ester, 2',4'-dimethoxydibenzoylmethane-4-carboxylic acid stearyl ester, 4'-tert-butyldibenzoylmethane-4-carboxylic acid-2-ethylhexyl ester, 4'-palmityldibenzoylmethane-4-carboxylic acid isopropyl ester, and the like.

The hydrous oxides of polyvalent metallic elements used according to another embodiment of the invention are hydrous oxides of di- through hexa-valent metallic elements such as, for example, magnesium, berylium, gallium, indium, iron (III), aluminum, lanthanum, manganese (III), antimony (III), bismuth (III), titanium (IV), tin (IV), zirconium, cerium (IV), thorium, silicon, manganese (IV), niobium, tantalum, antimony (V), molybdenum, tungsten, and the like.

The term "hydrous oxide" used herein may be also called hydrated oxides and means hydrates of metal oxides including so-called hydroxides as expressed by the general formula, $M_nO_m.xH_2O$ in which M represents a metal, n and m are independently an integrer, and x is a positive value. Examples of the hydrous oxides of polyvalent metallic elements include $BeO.1.7-H_2O$, $Mg(OH)_2$, $Ga_2O_3.2.4H_2O$, $In_2O_3. 3.5H_2O$, $Sb_2O_3.3H_2O$, $Bi_2O_3.3H_2O$, $La_2O_3.3H_2O$, $Fe_2O_3.2H_2$, beta-$Fe_2O_3. H_2O$, $Al_2O_3.3H_2O$, $Al_2O_3.1.2H_2O$, $Al_2O_3 H_2O$, $MnO.OH$, $MnO_2.0.6H_2O$, $SiO_2.1.2H_2O$, alpha-$TiO_2.1.6H_2O$, beta-$TiO_2.0.8H_2O$, $TiO_2.0.5H_2O$ (rutile), $ZrO_2.2.8H_2O$, alpha-$SnO_2.1.8H_2O$, beta-$SnO_2.1.6H_2O$, $CeO_2.2.6H_2O$, $ThO_2.3.5H_2O$, $Nb_2O_5.4.6H_2O$, $Ta_2O_5.3.4H_2O$, $Sb_2O_5.4H_2O$, $HBiO_3$, 1 $MoO_3.2H_2O$, $WO_3.3H_2O$, $WO_2.1.8H_2O$, and the like. Where these hydrous oxides are added to cosmetic compositions, hydrous oxides of aluminum, titanium, silicon and the like are preferred.

The UV-A absorber according to one embodiment of the invention is made by adding dibenzoylmethane derivatives (I) to a suitable carrier. The carrier should be inert to the dibenzoylmethane derivatives (I), and may be in the form of solid, liquid, emulsion, aerosol, gel and the like. Typical carriers include water, alcohols, oils and fats such as, for example, hydrocarbon oils, aliphatic acid esters, long-chain alcohols, silicone oils and the like, fine powders of starch, talc and the like, and low boiling hydrocarbons or halogenated hydrocarbons used as aerosol propellants. The UV-A absorber of the invention may further comprise other additives such as preservatives, perfumes, colorants, surfactants, and the like in amounts not impeding the UV-A absorbing action of the derivatives (I).

The dibenzoylmethane derivatives (I) whose carboxylic acid, -COOH, is suitably substituted with a group, X, have good affinity for various cosmetic substrates without impeding the UV-A absorption activity, so that the derivatives can be added to such substrates in order to impart UV-A absorbance. If X is a monovalent metal cation or an organic cation, the resulting derivatives are improved in solubility in water. On the other hand, when X is a hydrocarbon group, i.e. the resulting derivatives are esters, the derivatives may have a controlled HLB balance which depends on the number of carbon atoms in the hydrocarbon group. As a result, the derivatives can be controlled so that they have an optimum affinity for an intended cosmetic substrate. In addition, the HLB balance can appropriately be controlled by suitably changing the substituents, Y and Z, in the general formula (I). For instance, when a hydroxyl group or a polyethylene-oxide group is introduced, the resulting derivatives become soluble in water. The introduction of an alkoxy group or a polypropylene-oxide group results in an increase of fat solubility.

The UV-A and UV-B absorber according to the second embodiment of the invention is prepared, for example, by the following procedure. First, a volatile acid is added to an aqueous dispersion of a hydrous metal oxide to obtain a colloidal dispersion. Then, an aqueous solution of a dibenzoylmethane derivative is gradually added to the dispersion at room temperature and agitated. Alternatively, a powder or oil of the derivatives may be gradually added to the dispersion at room temperature and agitated. The resulting aqueous dispersion of the UV absorber composition may be used as it is, or may be dialyzed and/or washed with water, dried and ground into pieces, if necessary.

In the above procedure, the pH of the composition is preferred to be in the range of from 1 to 7, under which the composition is transparent to visible light and has thus small hiding capability, without involving any problems such as on use as cosmetics, e.g. whitening. The pH of the composition is preferably adjusted by the use of a volatile acid such as hydrochloric acid, nitric acid, acetic acid, formic acid or the like. It should be noted, however, that hydrous metal oxides exhibit the buffer action in a certain pH range, depending upon the type of metal oxide. The amount of the acid is preferred to be in the range of from 0.001 to 5 moles per mole of the hydrous metal oxide. Within the above-defined pH range of from 1 to 7, hydrous metal oxides are dispersed in colloidal form, with a colloid particle size of from 0.001 to 10 $\mu$m. In this condition, the colloid particles are positively charged on the surface thereof. The rate of travel of the colloid particles is preferred to be in the range of from 10 to $70 \times 10^5$ cm/second.

In the UV-A absorber composition of the invention, the amount of dibenozylmethane derivatives (I) may vary depending on the type of composition and is not critically determined, but an effective amount is necessary. In general, the derivative is used in an amount of from 0.1 to 20 wt% (hereinafter referred to as simply as %), preferably from 0.5 to 10%.

In the composition of the second embodiment in which a hydrous oxide of a polyvalent metallic element is further contained, the amount of the dibenzoylmethane derivative (I) may also vary depending on the type of final product and is not critically limited. In general, the amount is in the range of from 0.1 to 20%, preferably from 0.5 to 10%, of the total composition. The ratio by weight of the hydrous metal oxide to the dibenzoylmethane derivative is preferably in the range of from 0.01 to 100:1, most preferably from 0.5 to 10:1.

The long wavelength ultraviolet ray absorbers of the invention may be used in cosmetics. For the preparation of cosmetics, a dibenzoylmethane derivative (I) and/or a hydrous oxide of a polyvalent metallic element which has good affinity for a selected cosmetic substrate is first provided, followed by adding to the cosmetic substrate by a usual manner to obtain a cream, solution, oil, spray, stick, emulsion, foundation, or ointment.

In other words, the dibenzoylmethane derivative (I) and/or the hydrous oxide is suitably selected depending on the type of cosmetic substrate. In doing so, various types of cosmetics having the UV-A absorbance and/or UV-B absorbance can be prepared, including base cosmetics such as cosmetic oils using oil substrates, oily creams or oil rich emulsions, water rich creams or emulsions, and water-base lotions, foundations using oils as substrates, and makeup cosmetics such as lipsticks. The substrates and solvents suitable for the above purposes include, for example: hydrocarbons such as solid or liquid paraffin (crystal oil), ceresin, ozokerite, montan wax, and the like; plant oils or animal fats, oils and waxes such as olive oil, earth wax, carnauba wax, lanolin, spermaceti, and the like; fatty acids and esters thereof such as stearic acid, palmitic acid, oleic acid, glycerine monostearate, glycerine distearate, glycerine monooleate, isopropyl myristate, isopropyl stearate, butyl stearate, and the like; and alcohols such as ethyl alcohol, isopropyl alcohol, cetyl alcohol, stearyl alcohol, palmityl alcohol, hexyldodecyl alcohol, and the like. Additionally, polyvalent alcohols such as glycol, glycerine, sorbitol and the like may also be used.

The cosmetics may further contain effective UV-B absorbers, if desired. Examples of such other UV-B absorbers include p-methylbenzylidene-D,L-camphor and sodium sulfonate thereof, sodium 2-phenylbenzimidazole-5-sulfonate, sodium 3,4-dimethylphenylglyoxylate, 4-phenylbenzophenone, isooctyl 4-phenylbenzophenone-2'-carboxylates, p-methoxycinnamates, 2-phenyl-5methylbenzoxazole, p-dimethylaminobenzoates, and the like.

The cosmetics of the invention may comprise, aside from the above ingredients, various additives. Appropriate additives include, for example, W/O type or O/W type emulsifiers. Such emulsifiers may be any commercially available emulsifiers. Thickeners such as methyl cellulose, ethyl cellulose, carboxymethyl cellulose, polyacrylic acid, gum tragacanth, agar-agar, gelatin, and the like may be used as additives. If necessary, perfumes, preservatives, humectants, emulsification stabilizers, medical ingredients and/or physiologically acceptable colorants may be added.

As described hereinabove, the long wavelength UV absorbers of the invention can effectively absorb ultraviolet rays which will cause such harmful action as described before, and thus protect the skin from sunburning and are stable against light and heat over a long term. The UV absorbers of the present invention are not irritants, not percutaneously absorbable and are not easily removable by water or by sweat. In other words, the composition shows lasting effects.

The present invention is described in more detail by way of examples.

TEST EXAMPLE 1

Creams comprising 2% of dibenzoylmethane derivatives according to the invention were used to determine the effect of the derivatives serving to protect the skin from UV-A irradiation. In this test, a cream composition of Example 4 was used except that there were used, instead of 4'-methoxydibenzoylmethane-2-carboxylic acid, sodium 4'-methoxydibenzoylmethane-2-carboxylate (product 1 of the invention), sodium 3',4'-bis(- polyoxyethyleneoxy)dibenzoylmethane-3-carboxylate ($n_1=3$, which indicates the moles of added oxyalkylene group, product 2 of the invention), sodium 4'-methoxy-3'-polyoxyethyleneoxydibenzoylmethane-4-carboxylate ($n_1=4$, product 3 of the invention), isostearyl 4'-methoxy-4-methyldibenzoylmethane-2-carboxylate (product 4 of the invention), methyl 3',4'-bis(polyoxypropyleneoxy)dibenzoylmethane-2-carboxylate ($n_1=3$, product 5 of the invention), and isopropyl 4'-palmityldibenzoylmethane-4-carboxylate (product 6 of the invention). The test was carried out by the method as described by Gschnait et al (Archives of Dermatological Research 263, 181-188 (1978)). More particularly, guinea pigs were each shaved on the back thereof to expose the skin, followed by peritoneal administration of 8-methoxypsoralen in order to enhance susceptibility to UV-A. Subsequently, the exposed skin was applied with each of the products 1 to 6 of the invention in an amount of 2 mg/cm², followed by UV-A irradiation 15 minutes after the application. Twenty four hours after completion of the irradiation, the skin was visually observed to determine whether or not erythema appeared, and a minimum irradiation time before appearance of erythema on the skin was determined. This time was compared with a minimum UV-A irradiation time before erythema appeared on non-applied skin, and a sunlight protecting factor (hereinafter referred to simply as SPF) was calculated according to the following equation to determine the skin protection effect of each compound. The results are shown in FIG. 1. For comparison, a cream base of Example 4 (comparative product 1), and vaseline (comparative product 2) were used.

$$SPF = \frac{\text{Minimum UV-A irradiation time before erythema appears on the skin applied with a product of the invention}}{\text{Minimum UV-A irradiation time before erythema appears in the non-applied skin}}$$

From the results of this test, it will be seen that with the application of the cream base alone and vaseline, the skin cannot be protected from UV-A, whereas the creams comprising 2% of the dibenzoylmethane derivatives of the invention exhibit SPF values as high as 5 to 6, thus serving to effectively protect the skin from the UV-A light.

EXAMPLE 1

Lotion:

The following ingredients were mixed as usual to obtain a lotion.

Formulation:

| | |
|---|---|
| Sodium 3',4'-bis(polyoxyethyleneoxy)-dibenzoylmethane-3-carboxylate ($n_1 = 3$) | 2.0 wt % |
| Glycerine | 2.0 |
| Propylene glycol | 5.0 |
| Ethanol | 10.0 |
| Polyoxyethylene (20) hexadecyl ether | 1.0 |
| Purified water | 79.0 |
| Preservative | suitable amount |
| Perfume | suitable amount |
| Colorant | very small amount |

EXAMPLE 2

Milky Lotion:

The following ingredients were mixed as usual to obtain a milky lotion.

Formulation:

| | |
|---|---|
| Potassium 4'-methoxy-3'-polyoxyethyleneoxy-dibenzoylmethane-4-carboxylate ($n_1 = 4$) | 5.0 wt % |
| Stearic acid | 1.5 |
| Cetanol | 1.0 |
| Oleic monoglyceride | 0.5 |
| Vaseline | 2.0 |
| Liquid paraffin | 6.0 |
| Squalane | 6.0 |
| Purified water | 69.0 |
| Triethanolamine | 0.8 |
| Dipropylene glycol | 5.0 |
| Glycerine | 2.0 |
| Carboxyvinyl polymer | 0.2 |
| Preservative | suitable amount |
| Perfume | " |

EXAMPLE 3

Milky Lotion:

The following ingredients were mixed as usual to obtain a milky lotion.

Formulation:

| | |
|---|---|
| Isostearyl 4'-methoxy-4-methyldibenzoyl-methane-2-carboxylate | 1.5 wt % |
| Stearic acid | 2.4 |
| Stearyl alcohol | 0.5 |
| Cetanol | 1.0 |
| Isopropyl myristate | 10.0 |
| Liquid paraffin | 5.0 |
| Vaseline | 2.0 |
| Purified water | 71.0 |
| Triethanolamine | 1.0 |
| Glycerine | 5.0 |
| Preservative | suitable amount |
| Perfume | suitable amount |

EXAMPLE 4

Cream:

The following ingredient were mixed as usual to obtain a cream.

Formulation:

| | |
|---|---|
| 4'-Methoxybenzoylmethane-2-carboxylic acid | 2.0 wt % |
| Polyoxyethylene (20) sorbitan monooleate | 2.0 |
| Sorbitan monooleate | 2.0 |
| Isopropyl myristate | 18.0 |
| Squalane | 7.0 |
| 2-Ethylhexanoic triglyceride | 12.0 |
| Antioxidant | suitable amount |
| Purified water | 51.0 |
| Propylene glycol | 5.0 |
| Preservative | suitable amount |
| Perfume | " |

EXAMPLE 5

Oily foundation:

The following ingredients were mixed as usual to obtain an oily foundation.

Formulation:

| | |
|---|---|
| Methyl 3',4'-bis(polyoxypropyleneoxy)-dibenzoylmethane-2-carboxylate ($n_1 = 3$) | 5.0 wt % |
| 2-Ethylhexyl p-methoxycinnamate | 5.0 |
| Liquid paraffin | 15.0 |

-continued

| | |
|---|---|
| Isopropyl palmitate | 16.0 |
| Lanoline alcohol | 3.0 |
| Microcrystalline wax | 7.0 |
| Ozokerite | 8.0 |
| Candelilla wax | 0.5 |
| Preservative | suitable amount |
| Antioxidant | " |
| Perfume | " |
| Titanium oxide | 15.0 |
| Kaolin | 15.0 |
| Talc | 6.0 |
| Blood red | 1.5 |
| Yellow iron oxide | 2.0 |
| Black iron oxide | 0.5 |

EXAMPLE 6

Lipstick:
The following ingredients were mixed as usual to obtain a lipstick.
Formulation:

| | |
|---|---|
| Isopropyl 4'-palmityldibenzoylmethane-4-carboxylate | 2.0 wt % |
| p-Dimethylaminobenzoic acid | 2.0 |
| Castor oil | 41.5 |
| Hexadecyl alcohol | 25.0 |
| Lanoline | 4.0 |
| Beeswax | 5.0 |
| Candelilla wax | 7.0 |
| Carnauba wax | 6.0 |
| Antioxidant | suitable amount |
| Preservative | " |
| Titanium oxide | 2.0 |
| Red No. 202 | 0.5 |
| Red No. 204 | 2.5 |
| Red No. 227 Al lake | 2.5 |
| Orange No. 201 | 0.2 |
| Perfume | suitable amount |

TEST EXAMPLE 2

Long wavelength ultraviolet light absorbers were prepared using 4'-methoxydibenzoylmethane-2-carboxylic acid and a salt thereof and alpha-alumina monohydrate according to the invention, and the absorption effect thereof was determined.

Figure 2:
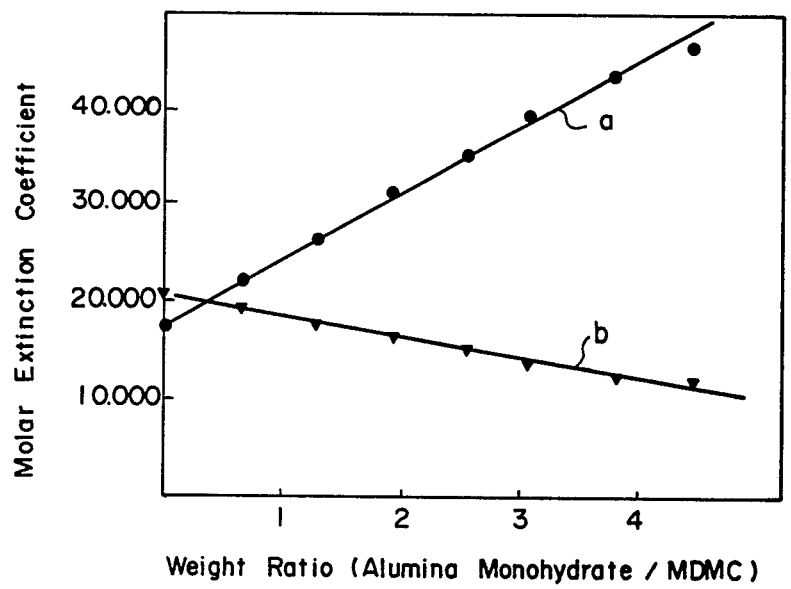
FIG. 2 is a graph showing a molar extinction coefficient of a mixture of 4'-methoxydibenzoylmethane-2-carboxylic acid (hereinafter referred to simply as MDMC) and alumina monohydrate in relation to the weight ratio of the alumina monohydrate to MDMC.
Figure 3:
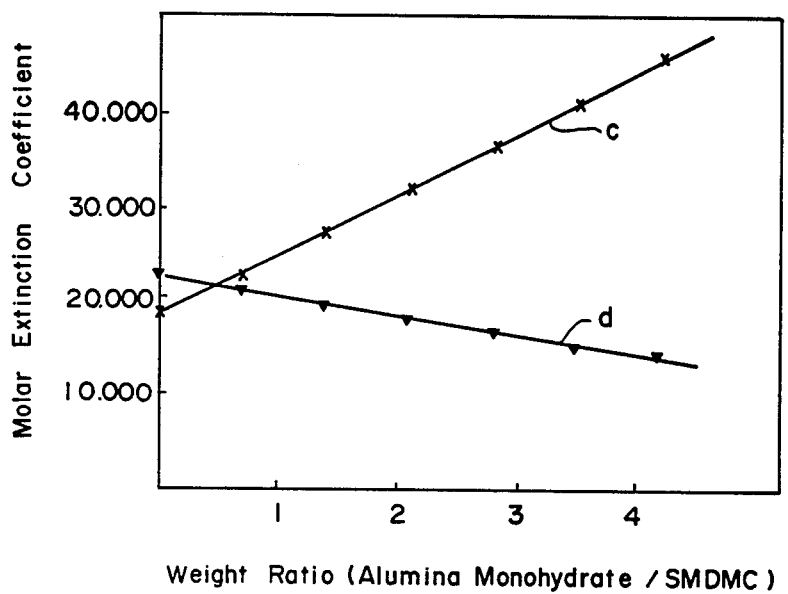
FIG. 3 is a graph showing a molar extinction coefficient of a mixture of sodium 4'-methyoxydibenzoylmethane-2-carboxylate (hereinafter referred to simply as SMDMC) and alumina monohydrate in relation to the weight ratio of the alumina monohydrate to SMDMC.
Figure 4:
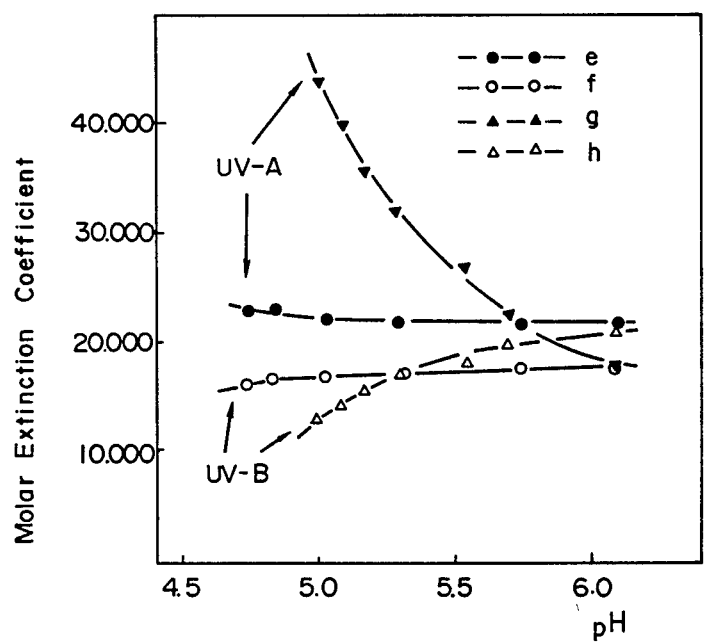
FIG. 4 is a graph showing an absorbance of mixtures of SMDMC with alumina monohydrate in relation to pH.

Alpha-alumina monohydrate was prepared by hydrolyzing aluminum triisopropoxide and adjusted in pH with hydrochloric acid, followed by mixing it with 4'-methoxydibenzoylmethane-2-carboxylic acid (MDMC) or a sodium salt thereof (SMDMC) in different weight ratios. The mixtures were each dispersion in water to determine an absorbance, from which a molal absorption factor of each UV absorber was determined. The results are shown in FIGS. 2 and 3, in which the abscissa axis indicates a ratio by weight of alpha-alumina monohydrate to an ultraviolet absorber and the ordinate axis indicates the molal absorption factor. In curve figures, the a indicates an absorption in an UV-A region at about 360 nm, and curve b indicates an absorption at about 290 nm, i.e. an absorption in an UV-B region. FIG. 4 shows a variation of the molal absorption factor in relation to pH of an absorber system using sodium 4'-dibenzoylmethane-carboxylate and alpha-alumina monohydrate. In the figure, curves e, g indicate absorptions in the UV-A region, and curves f, h indicate absorptions in the UV-B region. Moreover, curves e, f are the case where a ratio by weight of alpha-alumina monohydrate was kept at 1:1, whereas curves g, h are the case where the weight ratio of alpha-alumina monohydrate was changed from 0 to 4.2:1.

The absorptions in the UV-A and UV-B regions can be arbitrarily changed by changing the weight ratio of the dibenzoylmethane derivatives and the polyvalent hydrous metal oxide as will be clearly seen from FIGS. 2 and 3 and also by changing the pH of the system as will be seen from FIG. 4. Thus, if the weight ratio is defined in a certain range and/or the pH of the system is also defined, it becomes possible to effectively protect the skin from a total range of ultraviolet rays which give adverse influences on the skin.

Figure 5:
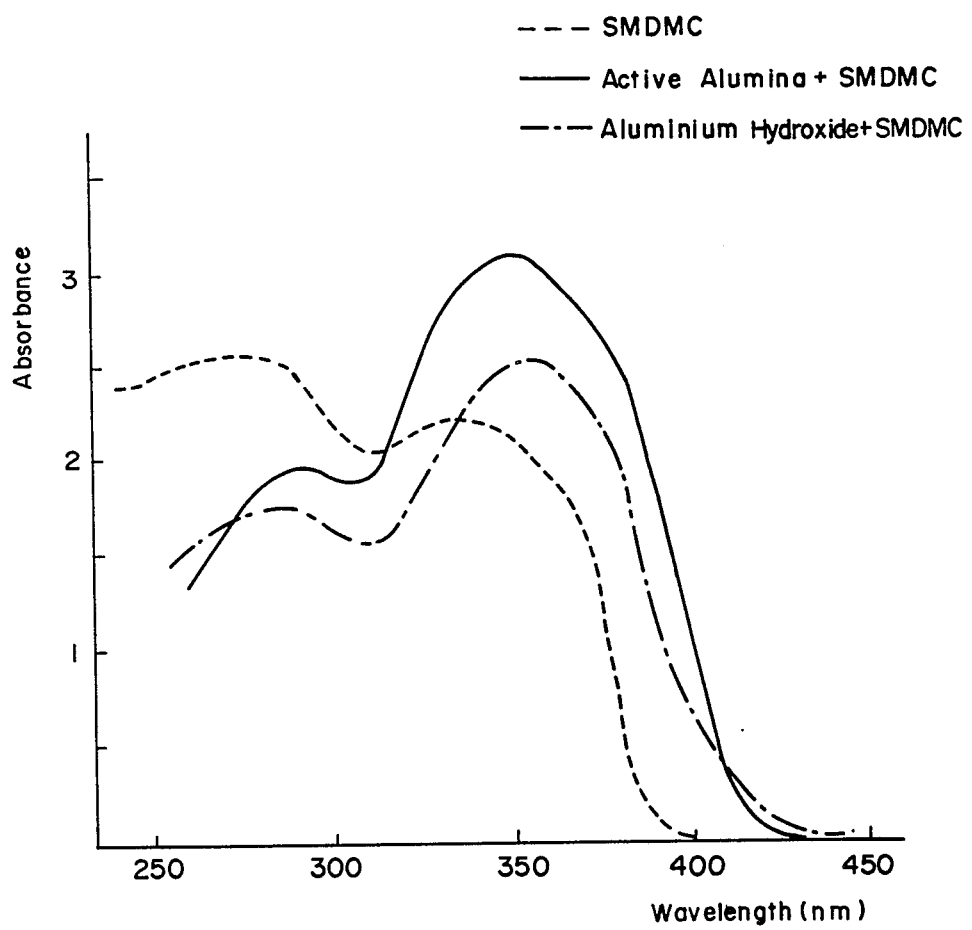
FIG. 5 is a graph showing an absorbance of SMDMC, mixtures of SMDMC with active alumina and aluminum hydroxide in relation to wavelength.

Not only alpha-alumina monohydrate, but also alumina hydrate having the formula, $Al_2O_3 \cdot xH_2O$ in which $x = 0.5$ to 3 can change the absorption in the UV-A and UV-B regions when mixed with the dibenzoylmethane derivatives. In FIG. 5, there are shown variations in absorbance of sodium 4'-methoxydibenzoylmethane-2-carboxylate, and mixtures of the carboxylate, with aluminum hydroxide or commercially available alumina ($Al_2O_3 \cdot xH_2O$) in a ratio by weight of 1:1. For the figure, it will be appreciated that the mixtures have similar absorptions in both UV-A and UV-B regions, and are thus useful in UV protection over a whole range of UV rays.

Figure 7:
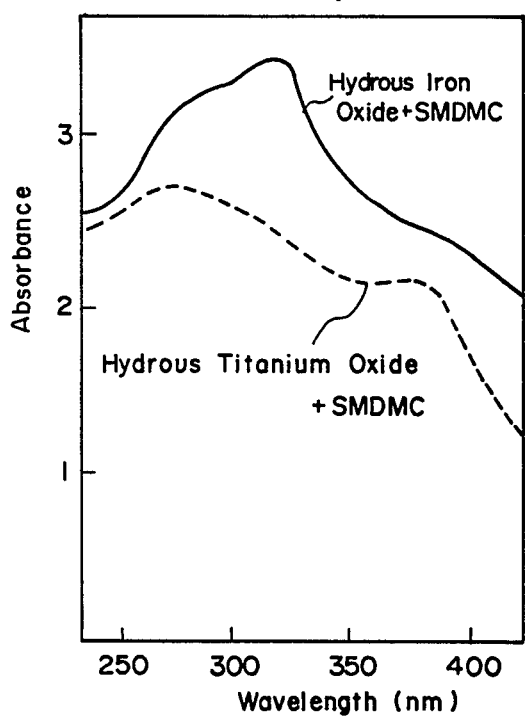
FIG. 7 is a graph showing a molar extinction coefficient of SMDMC mixed with hydrous iron oxide or hydrous titanium oxide in relation to wavelength.

The result of a test using, as the hydrous metal oxide, hydrous iron oxide and hydrous titanium oxide are shown in FIG. 6. From the results, it will be seen that when these hydrous metal oxides are used in combination with a dibenzoylmethane derivative (i.e. sodium 4'-methoxydibenzoylmethane-2-carboxylate) in varying weight ratios, the absorbance is also varied. The variation in absorbance of a composition having a ratio by weight of the hydrous metal oxide and the derivative at 1:1 is as shown in FIG. 7, revealing that a whole range of ultraviolet rays which are harmful against the skin can be shut out.

Figure 8:
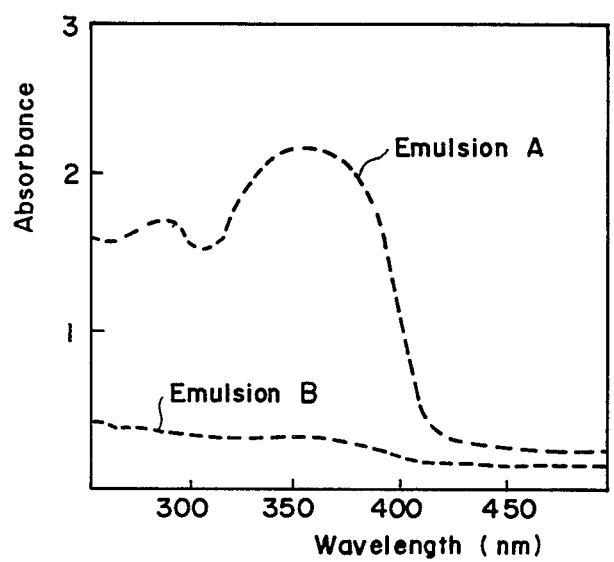
FIG. 8 is a graph showing an absorbance of emulsion A of the invention or emulsion B, indicated in Table 1, in relation to wavelength.

In order to check the UV-protective effect in more detail, a dibenzoylmethane derivative and a hydrous polyvalent metal oxide were added to an O/W-type emulsion by a usual manner to determine an absorbance. The measurement of the absorbance was effected as follows: the emulsion was applied onto a transparent quartz plate in a thickness of 30 μm, and subjected to spectrophotometer. The results are shown in FIG. 8, from which it will be seen that the whole range of UV rays which give harmful influences on the skin can be effectively protected.

Moreover, the emulsion comprising 4 wt % of an UV absorber composition according to the invention was used to determine the effect of protecting the skin from UV-A and UV-B irradiation. The UV-A protective effect was determined as follows: guinea pigs which had been peritoneally dosed with 8-methoxypsoralen and were thus sensitive UV-A were applied with the emulsion comprising the absorber of the invention. A minimum energy necessary for development of erythema one day after the UV-A irradiation was determined and compared with the case where no emulsion was applied. On the other hand, the UV-B protective effect was determined as follows: the emulsion comprising the absorber of the invention was applied to healthy men on the back thereof, and a minimum energy required for development of erythema one day after the UV-B irradiation, and compared with the case where no emulsion was applied. The comparison was made according to the following equation concerning sun protective factor (SPF).

$$SPF = \frac{\text{Minimum energy necessary for developing erythema on the skin applied with the emulsion comprising on absorber of the invention}}{\text{Minimum energy necessary for developing erythema on the one-applied skin}}$$

The formulations of the O/W-type emulsions are shown in Table 1 with the results shown in Table 2.

TABLE 1

|  | A (wt %) | B (wt %) |
|---|---|---|
| Stearic acid | 2.0 | 2.0 |
| Cetyl alcohol | 1.0 | 1.0 |
| Liquid paraffin | 20.0 | 20.0 |
| Polyoxyethylene(20) sorbitan stearate | 1.0 | 1.0 |
| Stearic monoglyceride | 1.0 | 1.0 |
| Alpha-$Al_2O_3.H_2O$ | 4.0 | — |
| Sodium 4'-methoxydibenzoylmethane-2-carboxylate | 4.0 | — |
| Propylene glycol | 5.0 | 5.0 |
| Purified water | balance | balance |
| Perfume, preservative | suitable amounts | suitable amounts |

TABLE 2

|  | SPF | |
|---|---|---|
|  | UV-A | UV-B |
| Emulsion A | 10.8 | 3.9 |
| Emulsion A | 0.8 | 0.9 |

TEST EXAMPLE 3

The stability of the present invention was determined as follows: an aqueous dispersion comprising 0.5 wt % of a composition of the invention was applied onto a transparent quartz plate in a thickness of 30 μm and subjected to measurement of an absorbance. In addition, an accelerated test was effected in such a way that a decomposition rate at 50° C. after 55 days was determined from a rate of reduction of the absorbance at about 360 nm. The results are shown in Table 3. Dibenzoylmethane derivatives having, for example, carboxyl groups therein are soluble in water and when such derivatives are dissolved in water and particularly under basic conditions, they undergo hydrolysis. However, when such derivatives are used in combination with hydrous oxides of polyvalent metallic elements, they become more stable. No discoloration such as blackening by application of light took place when the derivatives were exposed to sunlight.

TABLE 3

|  | Rate of Decomposition (50° C., 55 days) |
|---|---|
| Sodium 4'-methoxydibenzoylmethane-2-carboxylate + alpha $Al_2O_3.H_2O$ | 3% |
| Arginine dibenzoylmethane-2-carboxylate | 70% |
| Arginine 4'-methylbenzoylmethane-2-carboxylate | 63% |
| Potassium 4'-methoxydibenzoylmethane-2-carboxylate | 48% |
| Arginine 4'-ethoxydibenzoylmethane-2-carboxylate | 59% |

EXAMPLE 7

Lotion:
Formulaton:

| Sodium 3'-hydroxy-4'-methoxydibenzoyl-methane-2-carboxylate | 3% |
|---|---|
| Alpha-alumina monohydrate | 3% |
| Glycerine | 4% |
| Polyoxyethylene hardened castor oil | 2% |
| Ethanol | 10% |
| Preservative | suitable amount |
| Perfume | very small amount |
| Colorant | " |
| Purified water | balance |

EXAMPLE 8

Milky Lotion:
Formulation:

| 4'-Methoxy-3'-polyoxyethyleneoxydibenzoyl-methane-4-carboxylic acid | 3% |
|---|---|
| Alumina monohydrate | 3% |
| Stearic acid | 1% |
| Cetanol | 2% |
| Vaseline | 2.5% |
| Squalane | 4% |
| Hardened palm oil | 2% |
| Polyoxyethylene (20) sorbitan monostearate | 1.5% |
| Oleophilic glycerine monostearate | 1.2% |
| Glycerine | 3% |
| Potassium hydroxide | 0.2% |
| Carboxyvinyl polymer | 0.2% |
| Preservative | suitable amount |
| Perfume | very small amount |
| Purified water | balance |

EXAMPLE 9

O/W-type Cream:

| Arginine 4'-methoxydibenzoylmethane-2-carboxylate | 5% |
|---|---|
| Alumina monohydrate | 5% |
| Stearic acid | 2% |
| Cetanol | 4% |
| Vaseline | 5% |
| Squalane | 8% |
| Hardened palm oil | 4% |
| Polyoxyethylene (20) sorbitan monostearate | 2% |
| Sorbitan monostearate | 2% |
| Glycerine | 5% |
| Preservative | suitable amount |
| Perfume | very small amount |
| Purified water | balance |

EXAMPLE 10

Foundation Stick:
Formulation:

| Sodium 4'-polyoxyethylenoxydibenzoyl-methane-4-carboxylate | 5% |
|---|---|
| Titanium oxide hydrate | 5% |
| Hydrophobic titanium oxide | 10% |
| Kaolin | 15% |
| Talc | 10% |
| Liquid paraffin | 18% |
| Isopropyl myristate | 15% |
| Liquid lanoline | 4.5% |
| Microcrystalline wax | 4.5% |
| Ceresin wax | 10% |
| Carnauba wax | 2% |
| Sorbitan sesquioleate | 1% |

What is claimed is:

1. A long wavelength ultraviolet ray absorber composition comprsing 0.1 to 20 wt. % of a dibenzoylmethane derivative selected from the group consisting of

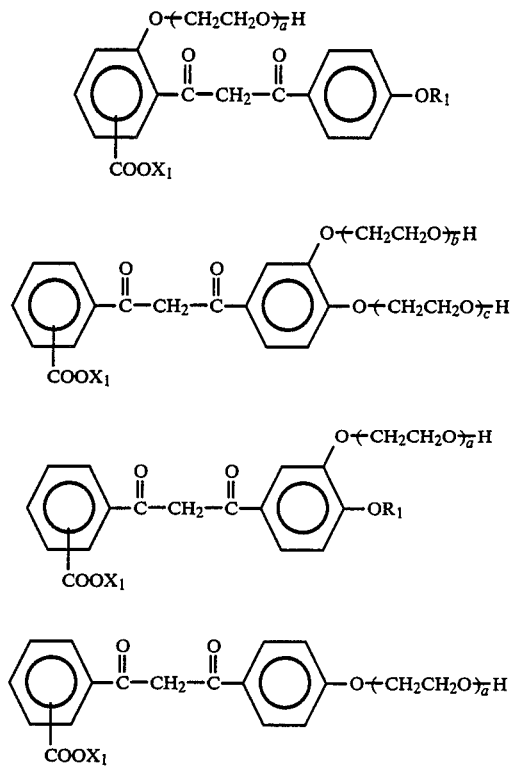

in which $X_1$ represents hydrogen, sodium, potassium, lithium, trimethylethanolamine, or arginine; $R_1$ represents a hydrogen atom, or a hydrocarbon group having from 1 to 18 carbon atoms; a is an integer of from 1 to 10, and c are independently integers of from 1 to 6; and an inert cosmetic carrier.

2. A long wavelength ultraviolet ray absorber composition comprising 0.1 to 20 wt. % of a dibenzoylmethane derivative of the formula

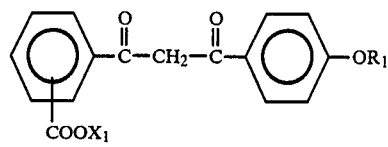

in which $R_1$ represents a hydrogen atom, or a hydrocarbon group having from 1 to 18 carbon atoms, and $X_1$ is hdyergoen, sodium, potassium, lithium, trimethylethanolamine, or arginine; and an inert cosmetic carrier.

3. A long wavelength ultraviolet ray absorber composition comprising 0.1 to 20 wt. % of a dibenzoylmethane derivative of the formula

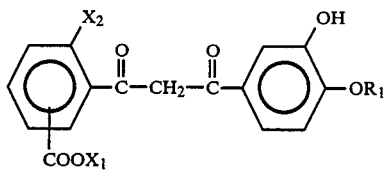

in which $X_1$ represents a hydrogen, sodium, potassium, lithium, trimethylethanolamine, or arginine, $X_2$ represents hydrogen or hydroxyl, and $R_1$ represents a hydrogen atom, or a hydrogen group having from 1 to 18 carbon atoms; and an inert cosmetic carrier.

4. The long wavelength ultraviolet ray absorber composition of any of claims 1-3, which further comprises a hydrous oxide of a polyvalent metallic element.

5. A method of preventing skin from aging or preventing enhancement or development of freckles, which comprises applying to said skin a composition according to any of claims 1-4.

* * * * *